United States Patent
Wilson et al.

(10) Patent No.: US 11,123,338 B2
(45) Date of Patent: Sep. 21, 2021

(54) C-MET MODULATOR PHARMACEUTICAL COMPOSITIONS

(71) Applicant: Exelixis, Inc., Alameda, CA (US)

(72) Inventors: Jo Ann Wilson, San Francisco, CA (US); Khalid Shah, Half Moon Bay, CA (US)

(73) Assignee: Exelixis, Inc., Alameda, CA (US)

( * ) Notice: Subject to any disclaimer, the term of this patent is extended or adjusted under 35 U.S.C. 154(b) by 0 days.

(21) Appl. No.: 16/722,563

(22) Filed: Dec. 20, 2019

(65) Prior Publication Data

US 2020/0121671 A1 Apr. 23, 2020

Related U.S. Application Data

(60) Continuation of application No. 16/026,708, filed on Jul. 3, 2018, now Pat. No. 10,548,888, which is a division of application No. 15/426,804, filed on Feb. 7, 2017, now Pat. No. 10,039,757, which is a division of application No. 13/810,537, filed as application No. PCT/US2011/044378 on Jul. 18, 2011, now Pat. No. 9,724,342.

(60) Provisional application No. 61/370,843, filed on Aug. 5, 2010, provisional application No. 61/365,253, filed on Jul. 16, 2010.

(51) Int. Cl.
| | | |
|---|---|---|
| *A61K 31/47* | (2006.01) | |
| *A61K 9/20* | (2006.01) | |
| *A61K 9/28* | (2006.01) | |
| *A61K 45/06* | (2006.01) | |

(52) U.S. Cl.
CPC ............ *A61K 31/47* (2013.01); *A61K 9/2009* (2013.01); *A61K 9/2013* (2013.01); *A61K 9/2018* (2013.01); *A61K 9/2054* (2013.01); *A61K 9/2095* (2013.01); *A61K 9/28* (2013.01); *A61K 9/2833* (2013.01); *A61K 9/2893* (2013.01); *A61K 45/06* (2013.01); *A61K 9/2866* (2013.01)

(58) Field of Classification Search
CPC ...... A61K 31/47; A61K 45/06; A61K 9/2018; A61K 9/2054; A61K 9/2866
See application file for complete search history.

(56) References Cited

U.S. PATENT DOCUMENTS

| | | |
|---|---|---|
| 7,579,473 B2 | 8/2009 | Bannen et al. |
| 7,977,345 B2 | 7/2011 | Bannen et al. |
| 7,999,006 B2 | 8/2011 | Lamb |
| 8,067,436 B2 | 11/2011 | Bannen et al. |
| 8,178,532 B2 | 5/2012 | Bannen et al. |
| 8,314,232 B2 | 11/2012 | Deschamps et al. |
| 8,476,298 B2 | 7/2013 | Bannen et al. |
| 8,497,284 B2 | 7/2013 | Bannen et al. |
| 8,673,912 B2 | 3/2014 | Cannon et al. |
| 8,877,776 B2 | 11/2014 | Brown et al. |
| 9,174,947 B2 | 11/2015 | Bannen et al. |
| 9,724,342 B2 | 8/2017 | Wilson et al. |
| 10,034,873 B2 | 7/2018 | Wilson et al. |
| 10,039,757 B2 | 9/2018 | Wilson et al. |
| 2005/0049267 A1 | 3/2005 | Suto et al. |
| 2005/0209247 A1 | 9/2005 | Cai et al. |
| 2007/0078159 A1 | 4/2007 | Matsushima et al. |
| 2008/0161305 A1 | 7/2008 | Forsyth et al. |
| 2009/0105299 A1* | 4/2009 | Bannen .............. A61K 31/4709 514/312 |
| 2009/0274693 A1 | 11/2009 | Gilmer et al. |
| 2011/0059081 A1 | 3/2011 | Bacus |
| 2011/0077233 A1 | 3/2011 | Bannen et al. |
| 2012/0070368 A1 | 3/2012 | Bannen et al. |
| 2012/0184523 A1 | 7/2012 | Bannen et al. |
| 2012/0252840 A1 | 10/2012 | Aftab et al. |
| 2012/0282179 A1 | 10/2012 | Aftab et al. |
| 2013/0030172 A1 | 1/2013 | Wilson et al. |
| 2013/0142790 A1 | 6/2013 | Gilmer et al. |
| 2013/0143881 A1 | 6/2013 | Cannon et al. |
| 2013/0150363 A1 | 6/2013 | Gilmer et al. |
| 2013/0197230 A1 | 8/2013 | Wilson et al. |
| 2013/0252940 A1 | 9/2013 | Bannen et al. |

(Continued)

FOREIGN PATENT DOCUMENTS

| | | |
|---|---|---|
| CN | 103221035 | 7/2013 |
| WO | 2005030140 | 1/2004 |
| WO | 2010083414 | 7/2010 |

OTHER PUBLICATIONS

European Medicines Agency, "Committee for orphan medicinal products Dec. 2008 plenary meeting monthly Yeport", Doc. Ref. EMEA/666785/2008 Corr. 2, Dec. 22, 2008.

(Continued)

*Primary Examiner* — Michael B. Pallay
(74) *Attorney, Agent, or Firm* — Honigman LLP; Heidi M. Berven

(57) ABSTRACT

Pharmaceutical compositions and unit dosage forms comprising Compound (I) are disclosed.

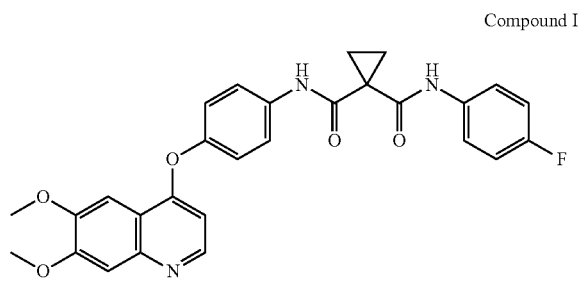

Compound I

27 Claims, No Drawings

(56) References Cited

U.S. PATENT DOCUMENTS

| | | |
|---|---|---|
| 2013/0252956 A1 | 9/2013 | Kallender et al. |
| 2013/0330377 A1 | 12/2013 | Wilson |
| 2014/0057908 A1 | 2/2014 | Smith et al. |
| 2014/0057943 A1 | 2/2014 | Smith et al. |
| 2014/0066444 A1 | 3/2014 | Smith et al. |
| 2014/0155396 A1 | 6/2014 | Bannen et al. |
| 2014/0179736 A1 | 6/2014 | Schwab et al. |
| 2014/0302012 A1 | 10/2014 | Aftab et al. |
| 2015/0057310 A1 | 2/2015 | Brown et al. |
| 2015/0196545 A1 | 7/2015 | Aftab et al. |
| 2015/0202196 A1 | 7/2015 | Bannen et al. |
| 2015/0376133 A1 | 12/2015 | Bannen et al. |
| 2016/0000772 A1 | 1/2016 | Aftab et al. |
| 2016/0051532 A1 | 2/2016 | Aftab et al. |
| 2016/0185725 A1 | 6/2016 | Bannen et al. |
| 2016/0220554 A1 | 8/2016 | Smith et al. |
| 2016/0229805 A1 | 8/2016 | Wilson et al. |
| 2017/0057921 A1 | 3/2017 | Wilson et al. |
| 2017/0275251 A1 | 9/2017 | Brown et al. |
| 2018/0311229 A1 | 11/2018 | Wilson et al. |

OTHER PUBLICATIONS

Handbook of Pharmaceutical excipients. Fifth Edition, 2006 pags. 132-135;211-213; 385-388; 336-339.

International Search Report for PCT/US2011/044378, dated Nov. 8, 2011.

Kurzrock R et al. "379 Poster A phase I study of XL 184, a MET, VEGFR2, and RET kinase inhibitor, administered orally to patients (pts) with advanced malignancies, including a subgroup of pts with medullary thyroid cancer (MTC)." Eropean journal of cancer, supplement, vol. 6, No. 12, Oct. 1, 2008, 119. (XP025534443).

Sigma-Aldrich Corporation, "Safety Data Sheet for 6,7-Dimethoxy-1H-Quinolin-4-One", Version 5.0, Oct. 20, 2014, retrieved from the internet at http://www.sigmaaldrich.com/MSDS/MSDS/DisplayMSDSPage.do?country=US&language=en&productNumber=CDS009101&brand=ALDRICH on Oct. 1, 2015.

United States Department of Health and Human Services, "Guidance for Industry Q1A(R2) Stability Testing of New Drug Substances and Products", Revision 2, Nov. 2003, retrieved from the internet at www.fda.gov/downloads/drugs/guidancecomplianceregulatory information/guidances/ucm073369.pdf on Oct. 1, 2015.

* cited by examiner

C-MET MODULATOR PHARMACEUTICAL COMPOSITIONS

CROSS-REFERENCE TO RELATED APPLICATIONS

This application is a divisional application of U.S. Ser. No. 16/026,708, filed Jul. 3, 2018, which is a divisional of U.S. Ser. No. 15/426,804, filed Feb. 7, 2017, which is a divisional of U.S. Ser. No. 13/810,537, filed Aug. 26, 2013, which is a 371 of international application number PCT/US2011/044378, filed Jul. 18, 2011, which claims the benefit of U.S. provisional patent application Ser. No. 61/370,843, filed Aug. 5, 2010, and which claims the benefit of U.S. provisional patent application Ser. No. 61/365,253, filed Jul. 16, 2010, all of which are incorporated herein by reference in their entirety.

FIELD OF THE INVENTION

Traditionally, dramatic improvements in the treatment of cancer are associated with identification of therapeutic agents acting through novel mechanisms. One mechanism that can be exploited in cancer treatment is the modulation of protein kinase activity. Signal transduction through protein kinase activation is responsible for many of the characteristics of tumor cells. Protein kinase signal transduction is particularly relevant in, for example, renal cancer, gastric cancer, head and neck cancers, lung cancer, breast cancer, prostate cancer, colorectal cancers, and hepatocellular carcinoma, as well as in the growth and proliferation of brain tumor cells.

Protein kinases can be categorized as receptor type or non-receptor type. Receptor-type tyrosine kinases are comprised of a large number of transmembrane receptors with diverse biological activity. For a detailed discussion of the receptor-type tyrosine kinases, see Plowman et al., DN&P 7(6): 334-339, 1994. Since protein kinases and their ligands play critical roles in various cellular activities, deregulation of protein kinase enzymatic activity can lead to altered cellular properties, such as uncontrolled cell growth that is associated with cancer. In addition to oncological indications, altered kinase signaling is implicated in numerous other pathological diseases, including, for example, immunological disorders, cardiovascular diseases, inflammatory diseases, and degenerative diseases. Protein kinases are therefore attractive targets for small molecule drug discovery. Particularly attractive targets for small-molecule modulation with respect to antiangiogenic and antiproliferative activity include receptor type tyrosine kinases c-Met, KDR, c-Kit, Axl, flt-3, and flt-4.

The kinase c-Met is the prototypic member of a subfamily of heterodimeric receptor tyrosine kinases (RTKs), which include Met, Ron, and Sea. The endogenous ligand for c-Met is the hepatocyte growth factor (HGF), a potent inducer of angiogenesis. Binding of HGF to c-Met induces activation of the receptor via autophosphorylation resulting in an increase of receptor dependent signaling, which promotes cell growth and invasion. Anti-HGF antibodies or HGF antagonists have been shown to inhibit tumor metastasis in vivo (See Maulik et al Cytokine & Growth Factor Reviews 2002 13, 41-59). c-Met overexpression has been demonstrated on a wide variety of tumor types, including breast, colon, renal, lung, squamous cell myeloid leukemia, hemangiomas, melanomas, astrocytomas, and glioblastomas. Additionally, activating mutations in the kinase domain of c-Met have been identified in hereditary and sporadic renal papilloma and squamous cell carcinoma. (See, e.g., Maulik et al, Cytokine & growth Factor reviews 2002 13, 41-59; Longati et al., Curr Drug Targets 2001, 2, 41-55; Funakoshi et al., Clinica Chimica Acta 2003 1-23).

Inhibition of epidermal growth factor (EGF), vascular endothelial growth factor (VEGF), and ephrin signal transduction will prevent cell proliferation and angiogenesis, both of which are key cellular processes needed for tumor growth and survival (Matter A., Drug Disc. Technol. 2001 6, 1005-1024). Kinase KDR (refers to kinase insert domain receptor tyrosine kinase) and flt-4 (fms-like tyrosine kinase-4) are both VEGF receptors. EGF and VEGF receptors are desirable targets for small molecule inhibition. All members of the VEGF family stimulate cellular responses by binding to tyrosine kinase receptors (the VEGFRs) on the cell surface, which causes them to dimerize and become activated through transphosphorylation. The VEGF receptors have an extracellular portion with immunoglobulin-like domains, a single transmembrane spanning region, and an intracellular portion containing a split tyrosine-kinase domain. VEGF binds to VEGFR-1 and VEGFR-2. VEGFR-2 is known to mediate almost all of the known cellular responses to VEGF.

Kinase c-Kit (also called stem cell factor receptor or steel factor receptor) is a type 3 receptor tyrosine kinase (RTK) that belongs to the platelet-derived growth factor receptor subfamily. Overexpression of c-Kit and c-Kit ligand has been described in variety of human diseases, including human gastrointestinal stromal tumors, mastocytosis, germ cell tumors, acute myeloid leukemia (AML), NK lymphoma, small-cell lung cancer, neuroblastomas, gynecological tumors, and colon carcinoma. Moreover, elevated expression of c-Kit may also relate to the development of neoplasia associated with neurofibromatosis type 1 (NF-1), mesenchymal tumors GISTs, and mast cell disease, as well as other disorders associated with activated c-Kit.

Kinase Flt-3 (fms-like tyrosine kinase-3) is constitutively activated via mutation, either in the juxtamembrane region or in the activation loop of the kinase domain, in a large proportion of patients with AML (acute myeloid leukemia) (See Reilly, Leuk. Lymphoma, 2003, 44: 1-7).

Accordingly, small-molecule compounds that specifically inhibit, regulate, and/or modulate the signal transduction of kinases, including c-Met, VEGFR2, KDR, c-Kit, Axl, flt-3, and flt-4, are particularly desirable as a means to treat or prevent disease states that are associated with abnormal cell proliferation and angiogenesis. One such small-molecule is Compound I, know also by its chemical name N-[4-[(6,7-Dimethoxy-4-quinolinyl)oxy]phenyl]-N'-(4-fluorophenyl)-1,1-cyclopropanedicarboxamide which has the following chemical structure.

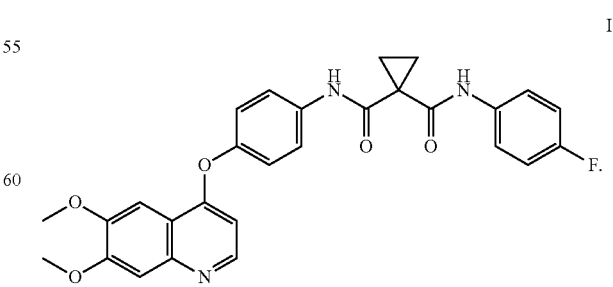

Compound I is disclosed and claimed in WO2005/030140, the entire contents of which is herein incorporated by reference. WO2005/030140 describes the synthesis of compound I (Table 2, Compound I2, Example 48) and discloses the therapeutic activity of this molecule to inhibit, regulate, and/or modulate the signal transduction of kinases (Assays, Table 4, entry 289). Compound I may be used as the malate salt.

Although therapeutic efficacy is the primary concern for a therapeutic agent, the pharmaceutical composition can be equally important to its development. Generally, drug developers endeavor to discover a pharmaceutical composition that possesses desirable properties, such as satisfactory water-solubility (including rate of dissolution), storage stability, hygroscopicity, and reproducibility, all of which can impact the processability, manufacture, and/or bioavailability of the drug. Accordingly, discovery of pharmaceutical compositions that possess some or all of these desired properties is vital to drug development.

SUMMARY OF THE INVENTION

These and other needs are met by the present disclosure, which is directed to a pharmaceutical composition comprising Compound I as provided in Table 1.

TABLE 1

| Ingredient | (% w/w) |
| --- | --- |
| Compound I | 31.68 |
| Microcrystalline Cellulose | 38.85 |
| Lactose anhydrous | 19.42 |
| Hydroxypropyl Cellulose | 3.00 |
| Croscarmellose Sodium | 3.00 |
| Total Intra-granular | 95.95 |
| Silicon dioxide, Colloidal | 0.30 |
| Croscarmellose Sodium | 3.00 |
| Magnesium Stearate | 0.75 |
| Total | 100.00 |

The disclosure is also directed to a pharmaceutical composition comprising Compound I as provided in Table 2.

TABLE 2

| Ingredient | (% w/w) |
| --- | --- |
| Compound I | 25.0-33.3 |
| Microcrystalline Cellulose | q.s |
| Hydroxypropyl Cellulose | 3 |
| Poloxamer | 0-3 |
| Croscarmellose Sodium | 6.0 |
| Colloidal Silicon Dioxide | 0.5 |
| Magnesium Stearate | 0.5-1.0 |
| Total | 100 |

The disclosure is further directed to a pharmaceutical composition comprising Compound I as provided in Table 3.

TABLE 3

| Ingredient | Theoretical Quantity (mg/unit dose) |
| --- | --- |
| Compound I | 100.0 |
| Microcrystalline Cellulose PH-102 | 155.4 |

TABLE 3-continued

| Ingredient | Theoretical Quantity (mg/unit dose) |
| --- | --- |
| Lactose Anhydrous 60M | 77.7 |
| Hydroxypropyl Cellulose, EXF | 12.0 |
| Croscarmellose Sodium | 24 |
| Colloidal Silicon Dioxide | 1.2 |
| Magnesium Stearate (Non-Bovine) | 3.0 |
| Opadry Yellow | 16.0 |
| Total | 416 |

In one aspect, Compound I is present in Tables 1, 2, and 3 as the L-malate salt.

The disclosure is also directed to a process of preparing a pharmaceutical composition according to Tables 1, 2, or 3.

The disclosure is further directed to a method for treating cancer, comprising administering to a patient in need of such treatment a pharmaceutical composition according to Tables 1, 2, or 3. The disclosure is also directed to a method for treating cancer, comprising administering to a patient in need of such treatment a pharmaceutical composition according to Tables 1, 2, or 3 in combination with another therapeutic agent.

In these and other treatment aspects, the cancers to be treated include the cancers disclosed in WO2005/030140, including pancreatic cancer, kidney cancer, liver cancer, prostate cancer, gastric cancer, gastroesophageal cancer, melanoma, lung cancer, breast cancer, thyroid cancer, and astrocytic tumors. More particularly, the cancers include pancreatic cancer, hepatocellular carcinoma (HCC), renal cell carcinoma, castration-resistant prostate cancer (CRPC), gastric or gastroesophageal junction cancer, melanoma, small cell lung cancer (SCLC), ovarian cancer, primary peritoneal or fallopian tube carcinoma, estrogen receptor positive breast cancer, estrogen receptor/progesterone receptor/HER2-negative (triple-negative) breast cancer, inflammatory (regardless of receptor status) breast cancer histology, non-small cell lung cancer (NSCLC), and medullary thyroid cancer.

DETAILED DESCRIPTION

The disclosure is directed to a pharmaceutical formulation comprising Compound I and pharmaceutically acceptable filler, binder, disintegrant, glidant, and lubricant, and optionally a film coating material, each of which are described in greater detail in the following paragraphs. Examples of pharmaceutically acceptable fillers, binders, disintegrants, glidants, lubricants, and film coatings are set forth below and are described in more detail in the Handbook of Pharmaceutical Excipients, Second Edition, Ed. A. Wade and P. J. Weller, 1994, The Pharmaceutical Press, London, England. The term excipient as used herein refers to inert materials which impart satisfactory processing and compression characteristics into the formulation or impart desired physical characteristics to the finished table.

Compound I Pharmaceutical Composition

The Compound I pharmaceutical composition is a tablet comprising Compound I and excipients selected from the group consisting of a filler, a binder, a disintegrant, a glidant, and a lubricant, and optionally may be coated or uncoated.

Compound I

In one embodiment, the pharmaceutical composition comprises Compound I as the free base.

In another embodiment, the pharmaceutical composition comprises Compound I as a hydrate.

In another embodiment, the pharmaceutical composition comprises Compound I as a salt.

In another embodiment, the salt of Compound I is the malate salt.

In another embodiment, the malate salt is the L-malate salt of Compound I, which has the following structure.

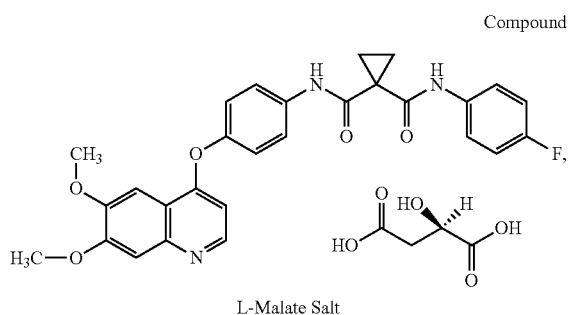

Compound I

L-Malate Salt

In a further embodiment, the malate salt is the D-malate salt. In a further embodiment, the malate salt is the D,L-malate salt.

The malate salts of Compound I, particularly the L malate salt, have a preferred combination of pharmaceutical properties for development. Under the conditions of 25° C./60 percent relative humidity (RH) and 40° C./60 percent RH, the L-malate salt of Compound I showed no change in assay, purity, moisture, and dissolution. The DSC/TGA showed the L-malate salt of Compound I to be stable up to 185° C. No solvent losses were observed. The uptake of water by the L-malate salt was reversible with a slight hysteresis. The amount of water taken up was calculated at about 0.60 weight percent at 90 percent RH. The L-malate salt was synthesized with good yield and purity greater than 90 percent and had sufficient solubility for use in a pharmaceutical composition. The amount of water associated with this salt was calculated at about 0.5 weight percent by Karl Fischer analysis and correlates with TGA and GVS analysis.

The L-malate salt of Compound I itself, and separately its crystalline and amorphous forms, exhibit beneficial properties over the free base and the other salts of Compound I. For example, the hydrochloride salt of Compound I exhibits undesirable moisture sensitivity, changing phase upon exposure to high humidity (75 percent RH) and high temperature (40° C.). The maleate salt had low solubility. The tartrate salt had low crystallinity and low solubility. The phosphate salt exhibited an 8 percent weight gain due to absorption of $H_2O$, the highest among the salts tested.

The water solubility of the various salts was determined using 10 mg solids per mL water. The salts were prepared in a salt screen by reacting an acetone solution of the free base with stock tetrahydrofuran (THF) solutions of a range of acids in about a 1:1 molar ratio. The table below summarizes the water solubility and other data relating to the free base and each salt.

| | Solubility (mg/ml) | |
|---|---|---|
| Free base | <<0.001 | very low solubility |
| Propionate | <<0.001 | no salt formation; mixture of free base and acid |
| Acetate | <<0.001 | no salt formation; mixture of free base and acid |
| Succinate | 0.010 | no salt formation; mixture of free base and acid |
| Benzoate | 0.005 | no salt formation; mixture of free base and acid |
| L-Lactate | 0.015 | Amorphous, salt |
| Pyroglutamate | 0.44 | Amorphous, salt |
| Glycolate | 0.016 | Amorphous, salt |
| L-Ascorbate | 0.053 | low crystallinity |
| Sulfate | 0.004 | Crystalline salt, low solubility |
| Tosylate | 0.007 | Crystalline salt, low solubility |
| Malonate | 0.003 | Crystalline salt, low solubility |
| 2,5dihydroxybenzoate | <<0.001 | Crystalline Salt, low solubility |
| Fumarate | 0.008 | Crystalline Salt, low solubility |
| Citrate | 0.002 | Crystalline Salt, low solubility |
| Mesylate | 0.175 | Crystalline Salt; possible sulfonic acid formation when made with alcohol |
| Esylate | 0.194 | Crystalline Salt; possible sulfonic acid formation when made with alcohol |
| Benzenesulfonate | 0.039 | Crystalline Salt; possible sulfonic acid formation when made with alcohol |
| Chloride | 0.070 | Crystalline but Hygroscopic; possible hydrate formation. Change in XRPD pattern upon exposure to humidity. |
| Maleate | 0.005 | Crystalline salt, possible hydrate formation; low solubility; different XRPD pattern observed upon scale up (possible polymorphism issue) |
| Phosphate | 0.026 | Crystalline but Hygroscopic. |
| L-Tartrate | 0.014 | Low degree of crystallinity; Hygroscopic. |
| L-Malate | 0.059 | Crystalline; non-Hygroscopic with no indication of hydrate formation. Suitable solubility, and chemical/physical stability. |

In another embodiment, the L-malate salt of Compound I is amorphous or in substantially amorphous form. "Substantially amorphous" means that more than 50 percent of the Compound I L-malate salt is amorphous.

In another embodiment, the L-malate salt of Compound I is crystalline or in substantially crystalline form. "Substantially crystalline" means that more than 50 percent of the L-malate salt of Compound I is crystalline. Two crystalline forms of the L-malate salt of Compound I are the N-1 and/or the N-2 crystalline forms.

Similarly, in another embodiment, the D-malate salt of Compound I is amorphous or in substantially amorphous form. "Substantially amorphous" means that more than 50 percent of the D-malate salt of Compound I is amorphous.

In another embodiment, the D-malate salt of Compound I is crystalline or in substantially crystalline form. "Substantially crystalline" means that more than 50 percent of the D-malate salt of Compound I is crystalline. Two crystalline forms of the D-malate salt of Compound I are the N-1 and/or the N-2 crystalline form.

Similarly, in another embodiment, the D,L-malate salt of Compound I is amorphous or in substantially amorphous form. "Substantially amorphous" means that more than 50 percent of the D,L-malate salt of Compound I is amorphous.

In another embodiment, the D,L-malate salt of Compound I is crystalline or in substantially crystalline form. "Substantially crystalline" means that more than 50 percent of the D,L-malate salt of Compound I is crystalline. Two crystalline forms of the D,L-malate salt of Compound I are the N-1 and/or the N-2 crystalline form.

As is known in the art, the crystalline D malate salt will form the same crystalline form and have the same properties as crystalline Compound I. See WO 2008/083319, which discusses the properties of crystalline enantiomers.

The crystalline N-1 form of the L-malate salt of Compound I and the N-1 form of the D-malate salt of Compound I may be characterized by at least one of the following:
  (i) a solid state $^{13}C$ NMR spectrum with peaks at 18.1, 42.9, 44.5, 70.4, 123.2, 156.2, 170.8, 175.7, and 182.1 ppm, ±0.2 ppm;
  (ii) an x-ray powder diffraction pattern (CuKα λ=1.5418 Å) comprising four or more peaks selected from: 6.4, 9.0, 12.0, 12.8, 13.5, 16.9, 19.4, 21.5, 22.8, 25.1, and 27.6°2θ±0.2°2θ, wherein measurement of the crystalline form is at an ambient room temperature;
  (iii) a solid state $^{15}N$ NMR spectrum with peaks at 118.6, 119.6, 120.7, 134.8, 167.1, 176.0, and 180 ppm, ±0.2 ppm; and/or Other solid state properties which may be used to characterize the crystalline N-1 forms of the L-malate salt of Compound I and the D-malate salt of Compound I are discussed in WO 2010/083414, the entire contents of which are incorporated herein by reference, and as described in the Examples below. For crystalline Compound I L-malate salt, the solid state phase and the degree of crystallinity remained unchanged after exposure to 75 percent RH at 40° C. for 1 week.

The crystalline N-2 forms of the L- and D-malate salts of Compound I as described here may be characterized by at least one of the following:
  (i) a solid state $^{13}C$ NMR spectrum with peaks at 23.0, 25.9, 38.0, 54.4, 56.11, 41.7, 69.7, 102.0, 122.5, 177.3, 179.3, 180.0, and 180.3, ±0.2 ppm;
  (ii) an x-ray powder diffraction pattern (CuKα λ=1.5418 Å) comprising four or more peaks selected from: 6.4, 9.1, 12.0, 12.8, 13.7, 17.1, 20.9, 21.9, 22.6, and 23.7°2θ±0.2°2θ, wherein measurement of the crystalline form is at an ambient room temperature;
  (iii) a solid state $^{15}N$ NMR spectrum with peaks at 118.5, 120.8, 135.1, 167.3, and 180.1 ppm.

Other solid state properties may be used to characterize the crystalline N-2 forms of the L- and D-malate salts of Compound I are discussed in WO 2010/083414.

In another embodiment, the crystalline form of the L-malate salt of Compound I, as described herein in any of the aspects and/or embodiments, is substantially pure N-1 form.

In another embodiment, the disclosure relates to a crystalline form of the L-malate salt of Compound I in substantially pure N-2 form.

Another aspect of this disclosure relates to crystalline forms of the D,L-malate salt of Compound I. The D,L-malate salt is prepared from racemic malic acid. The crystalline N-1 form of the D,L malate salt may be characterized by at least one of the following:
  (i) a solid state $^{13}C$ NMR spectrum with four or more peaks selected from 20.8, 26.2, 44.8, 55.7, 70.7, 100.4, 101.0, 114.7, 115.2, 116.0, 119.7, 120.4, 121.6, 124.4, 136.9, 138.9, 141.1, 145.7, 150.3, 156.5, 157.6, 159.6, 165.2, 167.4, 171.2, 176.3, 182.1 ppm, ±0.2 ppm;
  (ii) a powder x-ray diffraction pattern (CuKα λ=1.5418 Å) comprising four or more 2θ values selected from: 12.8, 13.5, 16.9, 19.4, 21.5, 22.8, 25.1, and 27.6, ±0.2°2θ, wherein measurement of the crystalline form is at temperature of room temperature; and/or
  (iii) a solid state $^{15}N$ NMR spectrum with peaks at 119.6, 134.7, and 175.5 ppm, ±0.2 ppm.

Other solid state properties may be used to characterize the crystalline N-1 form of the D,L malate salt of Compound I, as discussed in WO 2010/083414. In one embodiment, the N-1 Form of the D,L malate salt of Compound I is characterized by unit cell parameters approximately equal to the following:
Cell dimensions: a=14.60 Å
  b=5.20 Å
  c=39.09 Å
  α=90.0°
  β=90.4°
  γ=90.0°
Space group: $P2_1/n$
Molecules of Compound I/unit cell: 4
Volume=2969 Å$^3$
Density (calculated)=1.422 g/cm$^3$ The unit cell parameters of Form N-1 of the D,L malate salt of Compound I were measured at a temperature of approximately 25° C., e.g., ambient or room temperature.

Each of the N-1 and N-2 crystalline forms of the L-malate salt and the D-malate salt of Compound I and the crystalline form N-1 of the D,L malate salt of Compound I have unique characteristics that can distinguish them one from another. These characteristics can be understood by comparing the physical properties of the solid state forms. For example, Table 4 lists characteristic XRPD peak positions (°2θ±0.2°2θ) for the crystalline D,L malate salt of Compound I, Form N-1 and Forms N-1 and N-2 of the crystalline L-malate salt of Compound I. Amorphous forms do not display reflection peaks in their XRPD patterns.

TABLE 4

Characteristic diffraction peak positions (degrees 2θ ± 0.2) @ RT, based on pattern collected with a diffractometer (CuKα) with a spinning capillary.

| Compound I L-Malate Salt Form N-1 | Compound I L-Malate Salt Form N-2 | Compound (III) D,L Malate Salt Form N-1 |
|---|---|---|
| 6.4 | 6.4 | 6.4 |
| 9.0 | 9.1 | 9.1 |
| 12.0 | 12.0 | 12.1 |
| 12.8 | 12.8 | 12.8 |
| 13.5 | 13.7 | 13.6 |
| 16.9 | 17.1 | 17.1 |
| 19.4* | 20.9* | 19.3 |
| 21.5* | 21.9* | 21.4 |
| 22.8* | 22.6 | 22.8 |
| 25.1* | 23.7 | 25.1 |
| 27.6* | — | 27.6 |

*unique reflections between Compound I L-Malate Salt, Form N-1 and Compound I, L-Malate Salt, Form N-2.

The unique reflections between Forms N-1 and N-2 of the crystalline D-malate salt of Compound I are designated by an asterisk (*). As discussed above, the D-malate salt of Compound I is an enantiomer of the L-malate salt of Compound I and thus, Form N-1 of the D-malate salt of Compound I will have the same characteristic reflection pattern and unique peaks as those listed in Table 4 for the L-malate salt of Compound I, Form N-1. Likewise, Form N-2 of the D-malate salt of Compound I will have the same characteristic reflection pattern and unique peaks as those listed in Table 2 for the L-malate salt of Compound I, Form N-2. The L- and D-malate salts of Compound I are distinct from one another based on their absolute stereochemistry, i.e., the L-malate salt versus the D-malate salt, respectively. The crystalline D,L malate salt of Compound I, Form N-1, is distinct as the D,L-malate salt.

The characteristic peaks from the solid state NMR may also serve to distinguish the crystalline and amorphous forms disclosed herein. For example, Table 5 lists characteristic solid state $^{13}$C NMR peaks for the crystalline D,L-malate salt of Compound I, Form N-1, crystalline L-malate salt of Compound I, Forms N-1 and N-2, and the amorphous form of Compound I.

TABLE 5

Solid State Carbon-13 NMR Resonances (ppm, ±0.2 ppm)

| (I) Form N-1 | (I), Form N-2 | (III), Form N-1 | (I), Amorphous |
|---|---|---|---|
| 18.1 | 23.0 | 20.8 | 27.2 |
| 42.9 | 25.9 | 26.2 | 33.8 |
| 44.5 | 38.0 | 44.8 | 142.9 |
| 54.4 | 54.4 | 70.7 | — |
| 56.1 | 56.1 | 114.7 | — |
| 70.4 | 41.7 | 141.1 | — |
| 123.2 | 69.7 | 145.7 | — |
| 156.2 | 102.0 | 176.3 | — |
| 170.8 | 122.5 | 182.1 | — |
| 175.7 | 177.3 | — | — |
| 182.1 | 179.3 | — | — |
| — | 180.0 | — | — |
| — | 180.3 | — | — |

The solid state $^{19}$F and $^{15}$N NMR spectra, discussed below, provide data for similar comparison and characterization. As discussed above, being an enantiomer of the L-malate salt of Compound I, crystalline Forms N-1 and N-2 and the amorphous form of the D-malate salt of Compound I have the same solid state NMR resonances, and unique peaks between them, as those provided for Forms N-1 and N-2 of crystalline L-malate salt of Compound I.

The crystalline form of the L-malate salt and/or the D-malate salt of Compound I can occur as mixtures. The mixtures may have from greater than zero weight percent to less than 100 weight percent of the L-malate salt form and from less than 100 weight percent to greater than zero weight percent D-malate salt form, based on the total weight of L-malate salt form and D-malate salt form. In another embodiment, the mixture comprises from about 1 to about 99 weight percent of the L-malate salt form and from about 99 to about 1 weight percent of the D-malate salt form, based on the total weight of the L-malate salt form and the D-malate salt form in said mixture. In a further embodiment, the mixture comprises from about 90 weight percent to less than 100 weight percent L-malate salt form and from greater than zero weight percent to about 10 weight percent D-malate salt form, based on the total weight of the L-malate salt form and the D-malate salt form. Accordingly, the mixture may have 1 to 10 percent by weight of the L-malate salt form; 11 to 20 percent by weight of the L-malate salt form; 21 to 30 percent by weight of the L-malate salt form; 31 to 40 percent by weight of the L-malate salt form; 41 to 50 percent by weight of the L-malate salt form; 51 to 60 percent by weight of the L-malate salt form; 61 to 70 percent by weight of the L-malate salt form; 71 to 80 percent by weight of the L-malate salt form; 81 to 90 percent by weight of the L-malate salt form; or 91 to 99 percent by weight of the L-malate salt form with the remaining weight percentage of malate salt being that of the D-malate salt form.

Filler

As indicated above, the pharmaceutical composition containing Compound I comprises a filler. Fillers are inert ingredients added to adjust the bulk in order to produce a size practical for compression. Examples of fillers include sodium starch glycolate, corn starch, talc, sucrose, dextrose, glucose, lactose, xylitol, fructose, sorbitol, calcium phosphate, calcium sulfate, calcium carbonate, and the like, or mixtures thereof. Microcrystalline cellulose may also be used as a filler and may be any suitable form of microcrystalline cellulose as is known and used in the tabletting art. Preferably, a mixture of lactose and microcrystalline cellulose is used as the filler. In one embodiment, the lactose is anhydrous lactose sold as Lactose 60M, which is readily commercially available from a number of suppliers. In one embodiment, the microcrystalline cellulose is Avicel PH-102, which is also commercially available.

Preferably, filler(s) are present in an amount of from about 50 to about 70 percent, and more preferably from about 57 to about 67 percent, by weight on a solids basis of the directly compressible formulation. Preferably, lactose is present in an amount of from about 18 to 22 percent by weight. Preferably, the microcrystalline cellulose is present in an amount of from about 38 to 40 percent by weight.

Binder

The pharmaceutical composition containing Compound I also comprises a binder. Binders are added to powders to impart cohesive qualities to the powder, which allows the compressed tablet to retain its integrity. The binder can be any pharmaceutically acceptable binder available in the tabletting art, such as acacia, alginic acid, carbomer, carboxymethylcellulose sodium, dextrin, ethylcellulose, gelatin, guar gum, hydrogenated vegetable oil (type I), hydroxyethyl cellulose, hydroxypropyl cellulose, hydroxypropyl methylcellulose, liquid glucose, magnesium aluminum silicate, maltodextrin, methylcellulose, polymethacrylates, povidone, pregelatinized starch, sodium alginate, starch, zein, and the like, or mixtures thereof.

The preferred binder is hydroxypropyl cellulose preferably in an amount of from about 2 to about 4 percent by weight on a solid basis of the directly compressible formulation. In one embodiment, the hydroxypropyl cellulose is commercially available Klucel EXF.

Disintegrant

The pharmaceutical composition containing Compound I also comprises a disintegrant. A disintegrant is a substance or a mixture of substances added to facilitate breakup or disintegrate after administration. The disintegrant may be any pharmaceutically acceptable disintegrant available in the tabletting art, including alginic acid, carboxymethylcellulose calcium, carboxymethylcellulose sodium, colloidal silicon dioxide, croscarmellose sodium, crospovidone, guar gum, magnesium aluminum silicate, methylcellulose, microcrystalline cellulose, polyacrilin potassium, powdered cellulose, pregelatinized starch, sodium alginate, starch, and the like, or mixtures thereof.

The preferred disintegrant is croscarmellose sodium, in an amount of from about 4 to about 8 percent by weight, on a solid basis of the directly compressible formulation. In one embodiment, the croscarmellose sodium is commercially available Ac-Di-Sol.

Glidant

The pharmaceutical composition containing Compound I also comprises a glidant. The glidant may be any pharmaceutically acceptable glidant which contributes to the compressibility, flowability, and homogeneity of the formulation and which minimizes segregation and does not significantly interfere with the release mechanism of the binders as set forth above. Preferably, the glidant is selected to improve the flow of the formulation. Silicon dioxide, particularly colloidal silicon dioxide, is preferred as a glidant.

The glidant is used in an amount of from about 0.2 to about 0.6 percent by weight on a solid basis of the directly compressible formulation.

Lubricant

The pharmaceutical composition containing Compound I also comprises a lubricant. Lubricants are employed to prevent adhesion of the tablet material to the surface of dyes and punches. The lubricant may be any pharmaceutically acceptable lubricant which substantially prevents segregation of the powder by contributing to homogeneity of the formulation and which exhibits good flowability. Preferably, the lubricant functions to facilitate compression of the tablets and ejection of the tablets from the die cavity. Such lubricants may be hydrophilic or hydrophobic, and examples include magnesium stearate, Lubritab®, stearic acid, talc, and other lubricants known in the art or to be developed which exhibit acceptable or comparable properties, or mixtures thereof. Examples of lubricants include calcium stearate, glyceryl monostearate, glyceryl palmitostearate, hydrogenated castor oil, hydrogenated vegetable oil, light mineral oil, magnesium stearate, mineral oil, polyethylene glycol, sodium benzoate, sodium lauryl sulfate, sodium stearyl fumarate, stearic acid, talc, zinc stearate, and the like, or mixtures thereof.

The lubricant should be selected to aid in the flow of the powder in the hopper and into the die. Magnesium stearate exhibits excellent properties in combination with the other preferred excipients of the formulation. Magnesium stearate contributes to reducing friction between the die wall and tablet formulation during compression, as well as to the easy ejection of the Compound I tablets. It also resists adhesion to punches and dies.

Preferably, the lubricant is magnesium stearate (non-bovine) used in an amount of from about 0.5 to about 1.0 percent by weight on a solid basis of the directly compressible formulation.

Film Coating

The pharmaceutical composition containing Compound I also comprises an optional film coating. The film coat concentration can be about 1 to about 10 percent by weight on a solid basis of the directly compressible formulation. Film coating suspensions may include combinations of the following components: hypromeollose, carboxymethylcellulose sodium, carnauba wax, cellulose acetate phthalate, cetyl alcohol, confectioner's sugar, ethyl cellulose, gelatin, hydroxyethyl cellulose, hydroxypropyl cellulose, hydroxypropyl methylcellulose, liquid glucose, maltodextrin, methyl cellulose, microcrystalline wax, Opadry and Opadry II, polymethacrylates, polyvinyl alcohol, shellac, sucrose, talc, titanium dioxide, and zein.

Preferably the film coating comprises commercially available Opadry Yellow.

In one embodiment, the tablet composition comprises
30-32 percent by weight of Compound I in at least one of the forms disclosed herein;
50-70 percent by weight of a filler;
2-4 percent by weight of a binder;
4-8 percent by weight a disintegrant; and
0.2-0.6 percent by weight of a glidant; and 0.5-1 percent by weight of a lubricant.

In another embodiment, the tablet composition comprises:
30-32 percent by weight of Compound I in at least one of the forms disclosed herein;
50-70 percent by weight of a filler;
2-4 percent by weight of a binder;
4-8 percent by weight a disintegrant; and
0.2-0.6 percent by weigh of a glidant; and 0.5-1 percent by weight of a lubricant;
wherein the composition is coated.

In another embodiment, the tablet composition comprises:

| Component | Weight/Weight Percent |
|---|---|
| Compound I | 25-29 |
| Microcrystalline Cellulose | q.s. |
| Lactose Anhydrous | 40-44 |
| Hydroxypropyl Cellulose | 2-4 |
| Croscarmellose Sodium | 2-8 |
| Colloidal Silicon Dioxide | 0.1-0.4 |
| Magnesium Stearate | 0.7-0.9 |
| Total | 100 |

In another embodiment, the tablet compositions of this disclosure contain from 10 to about 200 mg of Compound I in at least one of the forms described herein. In another embodiment, the tablet compositions of this disclosure contain from 20 to 100 mg of Compound I. In another embodiment, the tablet compositions contain 20, 25, 50, 60, 75, 80, or 100 mg of Compound I.

In other embodiments, the tablet compositions are summarized in Tables 1, 2, and 3. The compound I used in these and other compositions disclosed herein is the L-malate salt Compound I. In the tables, the weight of Compound I refers to the amount of N-[4-[(6,7-Dimethoxy-4-quinolinyl)oxy]phenyl]-N'-(4-fluorophenyl)-1,1-cyclopropanedicarboxamide in the tablet. The skilled artisan will recognize that a certain amount of the Compound I L-malate salt is required to provide the weights listed in the tables. Thus, for example, in Table 3, 126.7 mg of Compound I L-malate salt is required to provide 100 mg of Compound I. Proportionally smaller or larger amounts of Compound I L-malate salt are required for tablet compositions containing less or more of Compound I.

Process

In another aspect, the disclosure is directed to a process for making pharmaceutical formulations comprising Compound I. In one embodiment, the formulation is a tablet formulation.

In another embodiment, the process comprises mixing Compound I with one or more of the pharmaceutical excipients. The mixture is then taken up in an aqueous solution containing a binder to form a binder solution. The binder solution is granulated using a granulation technique known in the art. For example, the granulation method may comprise wet high shear granulation using a wet high shear granulator. The resulting wet granules are then screened and dried using fluid bed drying or the like. The dried granules are then milled. The resulting dry milled granules are then mixed with a glidant and a disintegrant to form an extragranular blend. A lubricant is then blended into the extraganular blend to form the final blend. The final blend is subsequently compressed to form the compressed tablet, which may be film coated.

More particularly, the process comprises delumping Compound I as needed prior to mixing with the excipients. Delumping ensures that the Compound I mixes homogeneously with the other excipients during the formulation process. Delumped Compound I is then mixed with microcrystalline cellulose, such as Avicel PH102, lactose (anhydrous, 60M), and croscarmellose sodium. This mixture is then combined with EXF grade hydroxypropoyl cellulose in water to form a binder solution, which is then wet high shear granulated. The resulting wet granules are wet screened and then fluid bed dried according to methods available to the skilled artisan. The resulting dried granules are milled and combined with colloidal silicon dioxide and croscarmellose sodium. Magnesium stearate is added to the mixture. This final blend is then ready for tablet compression. The resulting uncoated core tablets are subsequently film coated. The film coating comprises Opadry Yellow, which contains hypromellose, titanium dioxide, triacetin, and iron oxide yellow.

More particularly, the formulation process comprises:
a) Delumping unmilled Compound I;
b) Premixing the delumped Compound I with Avicel PH102, lactose anhydrous 60M, and croscarmellose sodium to form a binder solution;
c) Wet high shear granulation of the binder solution to produce wet granules;
d) Wet screening of the wet granules to produce wet screened granules;
e) Fluid bed drying of the wet screened granules to produce dried granules;
f) Dry milling of the dried granules to produce dried milled granules;
g) Blending the dried milled granules with colloidal silicon and croscarmellose to produce an extragranular blend;
h) Lubricant blending of the extragranular blend and magnesium stearate to produce a final blend;
i) Tablet compression of the final blend to form an uncoated core tablet; and
j) Film coating of the uncoated core tablet.

Methods of Treatment

Another aspect of this disclosure relates to a method of treating cancer, using a pharmaceutical composition containing Compound I in at least one of its forms, either alone or in combination with another therapeutic agent. The cancer being treated is selected from stomach cancer, esophageal carcinoma, kidney cancer, liver cancer, ovarian carcinoma, cervical carcinoma, large bowel cancer, small bowel cancer, brain cancer (including astrocytic tumor, which includes glioblastoma, giant cell glioblastoma, gliosarcoma, and glioblastoma with oligodendroglial components), lung cancer (including non-small cell lung cancer), bone cancer, prostate carcinoma, pancreatic carcinoma, skin cancer, bone cancer, lymphoma, solid tumors, Hodgkin's disease, non-Hodgkin's lymphoma, or thyroid cancer (including medullary thyroid cancer). More particularly, the cancer is pancreatic cancer, hepatocellular carcinoma (HCC), renal cell carcinoma, castration-resistant prostate cancer (CRPC), gastric or gastroesophageal junction cancer, melanoma, small cell lung cancer (SCLC), ovarian cancer, primary peritoneal or fallopian tube carcinoma, estrogen receptor positive breast cancer, estrogen receptor/progesterone receptor/HER2-negative (triple-negative) breast cancer, inflammatory (regardless of receptor status) breast cancer, non-small cell lung cancer (NSCLC), or medullary thyroid cancer.

Tyrosine kinase inhibitors have also been used to treat non-small cell lung cancer (NSCLC). Gefitinib and erlotinib are angiogenesis inhibitors that target receptors of an epidermal growth factor called tyrosine kinase. Erlotinib and Gefitinib are currently being used for treating NSCLC. Another aspect of this disclosure relates to a method of treating non-small cell lung cancer (NSCLC) comprising administering to the subject in need of the treatment a therapeutically effective amount of Compound I in at least one of the forms described herein, pharmaceutically formulated as described herein, optionally in combination with Erlotinib or Gefitinib. In another embodiment, the combination is with Erlotinib.

In another embodiment, the cancer is non-small cell lung cancer (NSCLC), and the method comprises administering to the subject in need of the treatment a therapeutically effective amount of Erlotinib or Gefitinib in combination with at least one of the forms of Compound I in at least one of the forms described herein, pharmaceutically formulated as described herein. The method of treatment may be practiced by administering a tablet formulation of at Compound I in at least one of the forms described herein, pharmaceutically formulated as described herein.

Another aspect of this disclosure relates to a method of treating an astrocytic tumor (which includes glioblastoma, giant cell glioblastoma, gliosarcoma, and glioblastoma with oligodendroglial components) comprising administering to the subject in need of the treatment a therapeutically effective amount of Compound I in at least one of the forms described herein, pharmaceutically formulated as described herein.

Another aspect of this disclosure relates to a method of treating thyroid cancer (including medullary thyroid cancer) comprising administering to the subject in need of the treatment a therapeutically effective amount of Compound I in at least one of the forms described herein, pharmaceutically formulated as described herein.

Another aspect of this disclosure relates to a method of treating hepatocellular carcinoma comprising administering to the subject in need of the treatment a therapeutically effective amount of Compound I in at least one of the forms described herein, pharmaceutically formulated as described herein.

Another aspect of this disclosure relates to a method of treating renal cell carcinoma comprising administering to the subject in need of the treatment a therapeutically effective amount of Compound I in at least one of the forms described herein, pharmaceutically formulated as described herein.

Another aspect of this disclosure relates to a method of treating castration resistant prostate cancer comprising administering to the subject in need of the treatment a therapeutically effective amount of Compound I in at least one of the forms described herein, pharmaceutically formulated as described herein. The amount administered can be a therapeutically effective amount.

Another aspect of this disclosure relates to a method of breast cancer comprising administering to the subject in need of the treatment a therapeutically effective amount of Compound I in at least one of the forms described herein, pharmaceutically formulated as described herein.

Another aspect of this disclosure relates to a method of treating ovarian cancer comprising administering to the subject in need of the treatment a therapeutically effective amount of Compound I in at least one of the forms described herein, pharmaceutically formulated as described herein.

Another aspect of this disclosure relates to a method of treating diseases or disorders associated with uncontrolled, abnormal, and/or unwanted cellular activities. The method comprises administering to the subject in need of the treatment a therapeutically effective amount of Compound I in at least one of the forms described herein, pharmaceutically formulated as described herein.

A "therapeutically effective amount of the active compounds", or a crystalline or amorphous form of the active compound(s) to inhibit, regulate, and/or modulate the signal transduction of kinases (discussed here concerning the pharmaceutical compositions) refers to an amount sufficient to treat a patient suffering from any of a variety of cancers associated with abnormal cell proliferation and angiogenesis. A therapeutically effective amount according to this disclosure is an amount therapeutically useful for the treatment or prevention of the disease states and disorders discussed herein. Compound I possess therapeutic activity to inhibit, regulate, and/or modulate the signal transduction of kinases such as described in WO 2005/030140.

The actual amount required for treatment of any particular patient will depend upon a variety of factors, including the disease state being treated and its severity; the specific pharmaceutical composition employed; the age, body weight, general health, sex, and diet of the patient; the mode of administration; the time of administration; the route of administration; the rate of excretion of the active compound(s), or a crystalline form of the active compound(s), according to this disclosure; the duration of the treatment; any drugs used in combination or coincidental with the specific compound employed; and other such factors well known in the medical arts. These factors are discussed in Goodman and Gilman's "The Pharmacological Basis of Therapeutics," Tenth Edition, A. Gilman, J. Hardman and L. Limbird, eds., McGraw-Hill Press, 155-173, 2001, which is incorporated herein by reference. The active compound(s), or a crystalline form of active compound(s), according to this disclosure, and pharmaceutical compositions comprising them, may be used in combination with anticancer or other agents that are generally administered to a patient being treated for cancer. They may also be co-formulated with one or more of such agents in a single pharmaceutical composition.

EXAMPLES

The disclosure is illustrated further by the following examples in Scheme 1 and the description thereof, which are not to be construed as limiting the invention in scope or spirit to the specific procedures described in them. Those having skill in the art will recognize that the starting materials may be varied and additional steps employed to produce compounds encompassed by the invention, as demonstrated by the following examples. Those skilled in the art will also recognize that it may be necessary to utilize different solvents or reagents to achieve some of the above transformations.

Unless otherwise specified, all reagents and solvents are of standard commercial grade and are used without further purification. The appropriate atmosphere to run the reaction under, for example, air, nitrogen, hydrogen, argon and the like, will be apparent to those skilled in the art.

Example 1

Preparation of Compound I and Compound I and the L-Malate Salt of Compound I

A synthetic route that can be used for the preparation of N-(4-{[6,7-bis(methyloxy)quinolin-4-yl]oxy}phenyl)-N'-(4-fluorophenyl)cyclopropane-1,1-dicarboxamide and the L-malate salt thereof is depicted in Scheme 1.

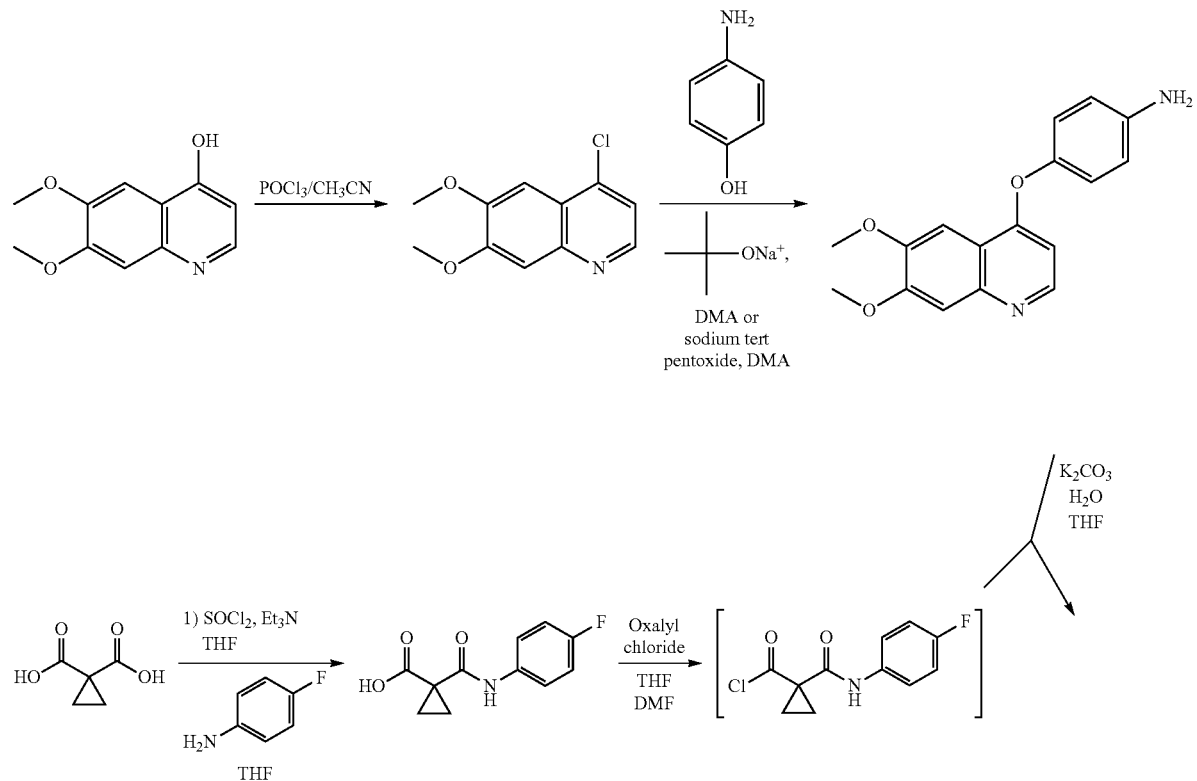

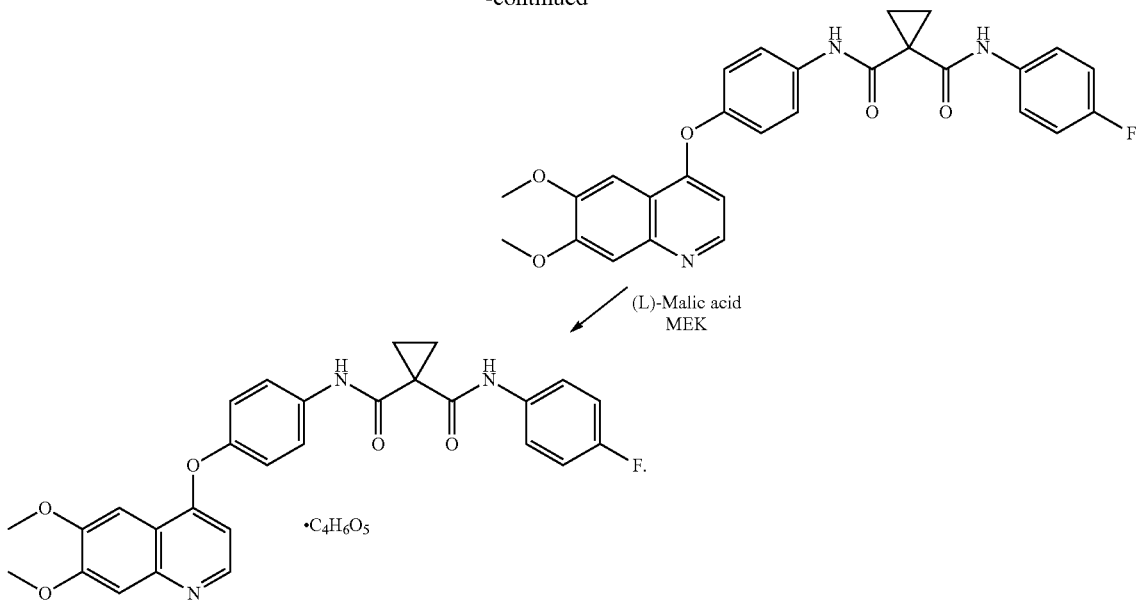

Preparation of 4-Chloro-6,7-dimethoxy-quinoline

A reactor was charged sequentially with 6,7-dimethoxy-quinoline-4-ol (47.0 kg) and acetonitrile (318.8 kg). The resulting mixture was heated to approximately 60° C., and phosphorus oxychloride (POCl$_3$, 130.6 kg) was added. After the addition of POCl$_3$, the temperature of the reaction mixture was raised to approximately 77° C. The reaction was deemed complete (approximately 13 hours) when less than 3% of the starting material remained (in-process high-performance liquid chromatography [HPLC] analysis). The reaction mixture was cooled to approximately 2-7° C. and then quenched into a chilled solution of dichloromethane (DCM, 482.8 kg), 26% NH$_4$OH (251.3 kg), and water (900 L). The resulting mixture was warmed to approximately 20-25° C., and phases were separated. The organic phase was filtered through a bed of AW hyflo super-cel NF (Celite™; 5.4 kg), and the filter bed was washed with DCM (118.9 kg). The combined organic phase was washed with brine (282.9 kg) and mixed with water (120 L). The phases were separated, and the organic phase was concentrated by vacuum distillation with the removal of solvent (approximately 95 L residual volume). DCM (686.5 kg) was charged to the reactor containing organic phase and concentrated by vacuum distillation with the removal of solvent (approximately 90 L residual volume). Methyl t-butyl ether (MTBE, 226.0 kg) was then charged, and the temperature of the mixture was adjusted to −20 to −25° C. and held for 2.5 hours, resulting in solid precipitate which was then filtered and washed with n-heptane (92.0 kg) and dried on a filter at approximately 25° C. under nitrogen to afford the title compound. (35.6 kg).

Preparation of 4-(6,7-Dimethoxy-quinoline-4-yloxy)-phenylamine

4-Aminophenol (24.4 kg) dissolved in N,N-dimethylacetamide (DMA, 184.3 kg) was charged to a reactor containing 4-chloro-6,7-dimethoxyquinoline (35.3 kg), sodium t-butoxide (21.4 kg), and DMA (167.2 kg) at 20-25° C. This mixture was then heated to 100-105° C. for approximately 13 hours. After the reaction was deemed complete as determined using in-process HPLC analysis (less than 2% starting material remaining), the reactor contents were cooled at 15-20° C., and water (pre-cooled, 2 to 7° C., 587 L) was charged at a rate to maintain 15-30° C. temperature. The resulting solid precipitate was filtered and washed with a mixture of water (47 L) and DMA (89.1 kg) and again with water (214 L). The filter cake was then dried at approximately 25° C. on filter to yield crude 4-(6,7-dimethoxy-quinoline-4-yloxy)-phenylamine (59.4 kg wet, 41.6 kg dry calculated based on LOD). Crude 4-(6,7-dimethoxy-quinoline-4-yloxy)-phenylamine was refluxed (approximately 75° C.) in a mixture of tetrahydrofuran (THF, 211.4 kg) and DMA (108.8 kg) for approximately 1 hour, then cooled to 0-5° C., and aged for approximately 1 hour, after which time the solid was filtered, washed with THF (147.6 kg), and dried on a filter under vacuum at approximately 25° C. to yield 4-(6,7-dimethoxy-quinoline-4-yloxy)-phenylamine (34.0 kg).

Alternative Preparation of 4-(6,7-Dimethoxy-quinoline-4-yloxy)-phenylamine 4-chloro-6,7-dimethoxyquinoline (34.8 kg), 4-Aminophenol (30.8 kg), and sodium tert pentoxide (1.8 equivalents) 88.7 kg, 35 wt percent in THF) were charged to a reactor, followed by N,N-dimethylacetamide (DMA, 293.3 kg). This mixture was then heated to 105-115° C. for approximately 9 hours. After the reaction was deemed complete as determined using in-process HPLC analysis (less than 2 percent starting material remaining), the reactor contents were cooled at 15-25° C., and water (315 kg) was added over a two hour period while maintaining the temperature between 20 and 30° C. The reaction mixture was then agitated for an additional hour at 20 to 25° C. The crude product was collected by filtration and washed with a mixture of water (88 kg) and DMA (82.1 kg), followed by water (175 kg). The product was dried on a filter drier for 53 hours. The LOD showed less than 1% weight/weight (w/w).

In an alternative procedure, 1.6 equivalents of sodium tert-pentoxide were used, and the reaction temperature was increased from 110-120° C. In addition, the cool down temperature was increased to 35-40° C., and the starting temperature of the water addition was adjusted to 35-40° C., with an allowed exotherm to 45° C.

Preparation of 1-(4-Fluoro-phenylcarbamoyl)-cyclopropanecarboxylic acid

Triethylamine (19.5 kg) was added to a cooled (approximately 5° C.) solution of cyclopropane-1,1-dicarboxylic acid (24.7 kg) in THF (89.6 kg) at a rate such that the batch temperature did not exceed 5° C. The solution was stirred for approximately 1.3 hours, and then thionyl chloride (23.1 kg) was added, keeping the batch temperature below 10° C. When the addition was complete, the solution was stirred for approximately 4 hours, keeping the temperature below 10° C. A solution of 4-fluoroaniline (18.0 kg) in THF (33.1 kg) was then added at a rate such that the batch temperature did not exceed 10° C. The mixture was stirred for approximately 10 hours, after which the reaction was deemed complete. The reaction mixture was then diluted with isopropyl acetate (218.1 kg). This solution was washed sequentially with aqueous sodium hydroxide (10.4 kg, 50 percent dissolved in 119 L of water) further diluted with water (415 L), then with water (100 L), and finally with aqueous sodium chloride (20.0 kg dissolved in 100 L of water). The organic solution was concentrated by vacuum distillation (100 L residual volume) below 40° C., followed by the addition of n-heptane (171.4 kg), which resulted in the precipitation of solid. The solid was recovered by filtration and washed with n-Heptane (102.4 kg), resulting in wet crude, 1-(4-fluoro-phenylcarbamoyl)-cyclopropanecarboxylic acid (29.0 kg). The crude, 1-(4-fluoro-phenylcarbamoyl)-cyclopropanecarboxylic acid was dissolved in methanol (139.7 kg) at approximately 25° C. followed by the addition of water (320 L), resulting in slurry which was recovered by filtration, washed sequentially with water (20 L) and n-heptane (103.1 kg), and then dried on the filter at approximately 25° C. under nitrogen to afford the title compound (25.4 kg).

Preparation of 1-(4-Fluoro-phenylcarbamoyl)-cyclopropanecarbonyl chloride

Oxalyl chloride (12.6 kg) was added to a solution of 1-(4-fluoro-phenylcarbamoyl)-cyclopropanecarboxylic acid (22.8 kg) in a mixture of THF (96.1 kg) and N, N-dimethylformamide (DMF; 0.23 kg) at a rate such that the batch temperature did not exceed 25° C. This solution was used in the next step without further processing.

Alternative Preparation of 1-(4-Fluoro-phenylcarbamoyl)-cyclopropanecarbonyl chloride A reactor was charged with 1-(4-fluoro-phenylcarbamoyl)-cyclopropanecarboxylic acid (35 kg), DMF (344 g), and THF (175 kg). The reaction mixture was adjusted to 12-17° C., and then to the reaction mixture was charged with oxalyl chloride (19.9 kg) over a period of 1 hour. The reaction mixture was left stirring at 12-17° C. for 3 to 8 hours. This solution was used in the next step without further processing.

Preparation of cyclopropane-1,1-dicarboxylic acid [4-(6,7-dimethoxy-quinoline-4-yloxy)-phenyl]-amide (4-fluoro-phenyl)-amide The solution from the previous step containing 1-(4-fluoro-phenylcarbamoyl)-cyclopropanecarbonyl chloride was added to a mixture of compound 4-(6,7-dimethoxy-quinoline-4-yloxy)-phenylamine (23.5 kg) and potassium carbonate (31.9 kg) in THF (245.7 kg) and water (116 L) at a rate such that the batch temperature did not exceed 30° C. When the reaction was complete (in approximately 20 minutes), water (653 L) was added. The mixture was stirred at 20-25° C. for approximately 10 hours, which resulted in the precipitation of the product. The product was recovered by filtration, washed with a pre-made solution of THF (68.6 kg) and water (256 L), and dried first on a filter under nitrogen at approximately 25° C. and then at approximately 45° C. under vacuum to afford the title compound (41.0 kg, 38.1 kg, calculated based on LOD).

Alternative Preparation of cyclopropane-1,1-dicarboxylic acid [4-(6,7-dimethoxy-quinoline-4-yloxy)-phenyl]-amide (4-fluoro-phenyl)-amide A reactor was charged with 4-(6,7-dimethoxy-quinoline-4-yloxy)-phenylamine (35.7 kg, 1 equivalent), followed by 412.9 kg THF. To the reaction mixture was charged a solution of 48.3 $K_2CO_3$ in 169 kg water. The acid chloride solution described in the Alternative Preparation of 1-(4-Fluoro-phenylcarbamoyl)-cyclopropanecarbonyl chloride above was transferred to the reactor containing 4-(6,7-dimethoxy-quinoline-4-yloxy)-phenylamine while maintaining the temperature between 20-30° C. over a minimum of two hours. The reaction mixture was stirred at 20-25° C. for a minimum of three hours. The reaction temperature was then adjusted to 30-25° C., and the mixture was agitated. The agitation was stopped, and the phases of the mixture were allowed to separate. The lower aqueous phase was removed and discarded. To the remaining upper organic phase was added water (804 kg). The reaction was left stirring at 15-25° C. for a minimum of 16 hours.

The product precipitated. The product was filtered and washed with a mixture of water (179 kg) and THF (157.9 kg) in two portions. The crude product was dried under a vacuum for at least two hours. The dried product was then taken up in THF (285.1 kg). The resulting suspension was transferred to reaction vessel and agitated until the suspension became a clear (dissolved) solution, which required heating to 30-35° C. for approximately 30 minutes. Water (456 kg) was then added to the solution, as well as SDAG-1 ethanol (20 kg) (ethanol denatured with methanol over two hours). The mixture was agitated at 15-25° C. for at least 16 hours. The product was filtered and washed with a mixture of 143 kg water (143 kg) and THF (126.7 kg) in two portions. The product was dried at a maximum temperature set point of 40° C.

In an alternative procedure, the reaction temperature during acid chloride formation was adjusted to 10-15° C. The recrystallization temperature was changed from 15-25° C. to 45-50° C. for 1 hour and then cooled to 15-25° C. over 2 hours.

Preparation of cyclopropane-1,1-dicarboxylic acid [4-(6,7-dimethoxy-quinoline-4-yloxy)-phenyl]-amide (4-fluoro-phenyl)-amide, (L) malate salt Cyclopropane-1,1-dicarboxylic acid [4-(6,7-dimethoxy-quinoline-4-yloxy)-phenyl]-amide (4-fluoro-phenyl)-amide (1-5; 13.3 kg), L-malic acid (4.96 kg), methyl ethyl ketone (MEK; 188.6 kg), and water (37.3 kg) were charged to a reactor, and the mixture was heated to reflux (approximately 74° C.) for approximately 2 hours. The reactor temperature was reduced to 50 to 55° C., and the reactor contents were filtered. These sequential steps described above were repeated two more times starting with similar amounts of 1-5 (13.3 kg), L-Malic acid (4.96 kg), MEK (198.6 kg), and water (37.2 kg). The combined filtrate was azeotropically dried at atmospheric pressure using MEK (1133.2 kg) (approximate residual volume 711 L; KF≤0.5% w/w) at approximately 74° C. The temperature of the reactor contents was reduced to 20 to 25° C. and held for approximately 4 hours, resulting in solid precipitate which was filtered, washed with MEK (448 kg), and dried under vacuum at 50° C. to afford the title compound (45.5 kg).

Alternative Preparation of cyclopropane-1,1-dicarboxylic acid [4-(6,7-dimethoxy-quinoline-4-yloxy)-phenyl]-amide (4-fluoro-phenyl)-amide, (L) malate salt Cyclopropane-1,1-dicarboxylic acid [4-(6,7-dimethoxy-quinoline-4-yloxy)-phenyl]-amide (4-fluoro-phenyl)-amide (47.9 kg), L-malic acid (17.2 kg), methyl ethyl ketone (658.2 kg), and water (129.1 kg) were charged to a reactor, and the mixture was heated 50-55° C. for approximately 1-3 hours, and then at 55-60° C. for an additional 4-5 hours. The mixture was clarified by filtration through a 1 µm cartridge. The reactor temperature was adjusted to 20-25° C. and vacuum distilled with a vacuum at 150-200 mm Hg with a maximum jacket temperature of 55° C. to the volume range of 558-731 L.

The vacuum distillation was performed two more times with the charge of 380 kg and 380.2 kg methyl ethyl ketone, respectively. After the third distillation, the volume of the batch was adjusted to 18 v/w of cyclopropane-1,1-dicarboxylic acid [4-(6,7-dimethoxy-quinoline-4-yloxy)-phenyl]-amide (4-fluoro-phenyl)-amide by charging methyl ethyl ketone (159.9 kg) to give a total volume of 880 L. An additional vacuum distillation was carried out by adjusting methyl ethyl ketone (245.7 kg). The reaction mixture was left with moderate agitation at 20-25° C. for at least 24 hours. The product was filtered and washed with methyl ethyl ketone 415.1 kg) in three portions. The product was dried under a vacuum with the jacket temperature set point at 45° C.

In an alternative procedure, the order of addition was changes so that a solution of L-malic acid (17.7 kg) dissolved in water (129.9 kg) was added to Cyclopropane-1,1-dicarboxylic acid [4-(6,7-dimethoxy-quinoline-4-yloxy)-phenyl]-amide (4-fluoro-phenyl)-amide (48.7 kg) in methyl ethyl ketone (673.3 kg).

General Methods of Analysis of Crystalline Forms of Compound I and Compound I, Malate Salt Crystalline forms may be prepared by a variety of methods including, but not limited to, crystallization or recrystallization from a suitable solvent mixture, sublimation, growth from a melt, solid state transformation from another phase, crystallization from a supercritical fluid, and jet spraying. Techniques for crystallization or recrystallization of crystalline forms of a solvent mixture include, but are not limited to, evaporation of the solvent, decreasing the temperature of the solvent mixture, crystal seeding of a supersaturated solvent mixture of the compound and/or salt thereof, crystal seeding a supersaturated solvent mixture of the compound and/or a salt from thereof, freeze drying the solvent mixture, and adding antisolvents (countersolvents) to the solvent mixture. High throughput crystallization techniques may be employed to prepare crystalline forms including polymorphs.

Crystals of drugs, including polymorphs, their methods of preparation, and the characterization of drug crystals, are discussed in Solid-State Chemistry of Drugs, S. R. Byrn, R. R. Pfeiffer, and J. G. Stowell, $2^{nd}$ Edition, SSCI, West Lafayette, Ind. (1999).

In a crystallization technique in which a solvent is employed, the solvent is typically chosen based on one or more factors including, but not limited to, solubility of the compound, crystallization technique utilized, and vapor pressure of the solvent. Combinations of solvents may be employed. For example, the compound may be solubilized in a first solvent to afford a solution, followed by the addition of an antisolvent to decrease the solubility of the compound in the solution and precipitate the formation of crystals. An antisolvent is a solvent in which a compound has low solubility.

In one method that can be used in preparing crystals, the L-malate salt of Compound I can be suspended and/or stirred in a suitable solvent to afford a slurry, which may be heated to promote dissolution. The term "slurry," as used herein, means a saturated solution of the compound, wherein such solution may contain an additional amount of compound to afford a heterogeneous mixture of compound and solvent at a given temperature.

Seed crystals may be added to any crystallization mixture to promote crystallization. Seeding may be employed to control growth of a particular polymorph and/or to control the particle size distribution of the crystalline product. Accordingly, calculation of the amount of seeds needed depends on the size of the seed available and the desired size of an average product particle as described, for example, in Programmed Cooling Batch Crystallizers," J. W. Mullin and J. Nyvlt, Chemical Engineering Science, 1971, 26, 3690377. In general, seeds of small size are needed to effectively control the growth of crystals in the batch. Seeds of small size may be generated by sieving, milling, or micronizing large crystals, or by microcrystallizing a solution. In the milling or micronizing of crystals, care should be taken to avoid changing crystallinity from the desired crystalline form (i.e., changing to an amorphous or other polymorphic form).

A cooled crystallization mixture may be filtered under vacuum and the isolated solid product washed with a suitable solvent, such as, for example, cold recrystallization solvent. After washing, the product may be dried under a nitrogen purge to afford the desired crystalline form. The product may be analyzed by a suitable spectroscopic or analytical technique including, but not limited to, differential scanning calorimetry (DSC), x-ray powder diffraction (XRPD), and thermogravimetric analysis (TGA), to ensure that the crystalline form of the compound has been formed. The resulting crystalline form may be produced in an amount greater than about 70 weight percent isolated yield, based on the weight of the compound originally employed in the crystallization procedure, and preferably greater than about 90 weight percent isolated yield. Optionally, the product may be delumped by comilling or passing through a mesh screen.

Preparation of Crystalline L-Malate Salt of Compound I

The preparation of the captioned salt and its characterization is described above and in WO 2010/083414, the entire contents of which is incorporated by reference.

Solid State Nuclear Magnetic Resonance (SSNMR)

All solid-state $^{13}C$ NMR measurements were made with a Bruker DSX-400, 400 MHz NMR spectrometer. High resolution spectra were obtained using high-power proton decoupling, the TPPM pulse sequence, and ramp amplitude cross-polarization (RAMP-CP) with magic-angle spinning (MAS) at approximately 12 kHz (A. E. Bennett et al, *J. Chem. Phys.*, 1995, 103, 6951 and G. Metz, X. Wu and S. O. Smith, *J. Magn. Reson. A*, 1994, 110, 219-227). Approximately 70 mg of sample, packed into a canister-design zirconia rotor, was used for each experiment. Chemical shifts (δ) were referenced to external adamantane with the high frequency resonance being set to 38.56 ppm (W. L. Earl and D. L. VanderHart, *J. Magn. Reson.*, 1982, 48, 35-54).

L-Malate Salt of Compound I

The solid state $^{13}C$ NMR spectrum of the crystalline L-malate salt of Compound I provides the following list of peaks, or a subset thereof, may be sufficient to characterize crystalline L-malate salt of Compound I.

SS $^{13}C$ NMR Peaks: 18.1, 20.6, 26.0, 42.9, 44.5, 54.4, 55.4, 56.1, 70.4, 99.4, 100.1, 100.6, 114.4, 114.9, 115.8, 119.6, 120.1, 121.6, 123.2, 124.1, 136.4, 138.6, 140.6, 145.4, 150.1, 150.9, 156.2, 157.4, 159.4, 164.9, 167.1, 170.8, 175.7, and 182.1 ppm, ±0.2 ppm.

The solid state $^{15}N$ NMR spectrum of the crystalline L-malate salt of Compound I. provides peaks at 118.6, 119.6, 120.7, 134.8, 167.1, 176.0, and 180 ppm, ±0.2 ppm. The entire list of peaks, or a subset thereof, may be sufficient to characterize crystalline L-malate salt of Compound I.

The solid state $^{19}F$ NMR spectrum of the crystalline L-malate salt of Compound I. provides peaks at −121.6, −120.8, and −118.0 ppm, ±0.2 ppm.

Thermal Characterization Measurements

Thermal Gravimetric Analysis (TGA)

TGA measurements were performed in a TA Instruments™ model Q500 or 2950, employing an open pan setup. The sample (about 10-30 mg) was placed in a previously tared platinum pan. The weight of the sample was measured accurately and recorded to a thousand of a milligram. The furnace was purged with nitrogen gas at 100 mL/min. Data were collected between room temperature and 300° C. at 10° C./min heating rate.

Differential Scanning Calorimetry (DSC) Analysis

DSC measurements were performed in a TA Instruments™ models Q2000, 1000, or 2920, employing an open pan setup. The sample (about 2-6 mg) was weighed in an aluminum pan, accurately recorded to a hundredth of a milligram, and transferred to the DSC. The instrument was purged with nitrogen gas at 50 mL/min. Data were collected between room temperature and 300° C. at a 10° C./min heating rate. The plot was made with the endothermic peaks pointing down.

L-Malate Salt of Compound I

The TGA thermogram for the crystalline L-malate salt of Compound I, which shows a weight loss of approximately 0.4 weight percent at a temperature of 170° C.

The DSC thermogram for the crystalline L-malate salt of Compound I, which showed a melting point of approximately 187° C.

Moisture Vapor Isotherm Measurements

Moisture sorption isotherms were collected in a VTI SGA-100 Symmetric Vapor Analyzer using approximately 10 mg of sample. The sample was dried at 60° C. until the loss rate of less than or equal to 0.0005 weight percent per minute was obtained for 10 minutes. The sample was tested at 25° C. and a relative humidity (RH) of 3, 4, 5, 15, 25, 35, 45, 50, 65, 75, 85, and 95 percent. Equilibration at each RH was reached when the rate of less than or equal to 0.0003 weight percent per minute for 35 minutes was achieved, or at a maximum of 600 minutes.

All ranges disclosed herein are inclusive of the endpoints, and the endpoints are independently combinable with each other.

The use of the terms "a", "an", "the", and similar referents in the context of describing the invention (especially in the context of the following claims) are to be construed to cover both the singular and the plural, unless otherwise indicated herein or clearly contradicted by context. Further, it should be noted that the terms "first," "second," and the like herein do not denote any order, quantity, or importance, but rather are used to distinguish one element from another. The modifier "about" used in connection with a quantity is inclusive of the stated value and has the meaning dictated by the context (e.g., it includes the degree of error associated with measurement of the particular quantity).

The foregoing disclosure has been described in some detail by way of illustration and example, for purposes of clarity and understanding. The invention has been described with reference to various specific and preferred embodiments and techniques. However, it should be understood that many variations and modifications can be made while remaining within the spirit and scope of the invention. It will be obvious to one of skill in the art that changes and modifications can be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

What is claimed is:

1. A method of treating cancer, wherein the cancer is selected from non-small cell lung cancer and prostate cancer, comprising administering to a patient in need of such treatment a tablet pharmaceutical composition comprising:
   30-32 percent by weight of Compound I, L-malate salt wherein Compound I is:

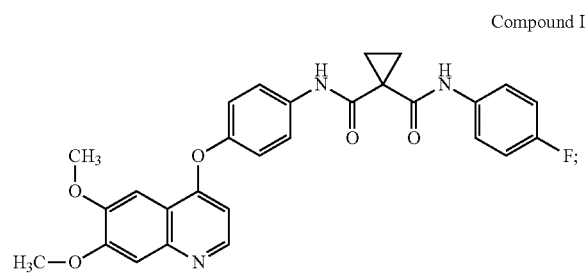 [SMILES: COc1cc2nccc(Oc3ccc(NC(=O)C4(C(=O)Nc5ccc(F)cc5)CC4)cc3)c2cc1OC]

Compound I 38-40 percent by weight of microcrystalline cellulose;
18-22 percent by weight of lactose;
2-4 percent by weight of hydroxypropyl cellulose;
4-8 percent by weight of croscarmellose sodium;
0.2-0.6 percent by weight of colloidal silicon dioxide; and
0.5-1 percent by weight of magnesium stearate;
alone or in combination with another therapeutic agent.

2. The method of claim 1, wherein the lactose in the tablet pharmaceutical composition is lactose anhydrous.

3. The method of claim 1, wherein the tablet pharmaceutical composition further comprises a film coating containing hypromellose, titanium dioxide, triacetin, and iron oxide yellow.

4. The method of claim 1, wherein the tablet pharmaceutical composition contains 20 to 100 mg of Compound I.

5. The method of claim 1, wherein the tablet pharmaceutical composition contains 20, 25, 50, 60, 75, 80, or 100 mg of Compound I.

6. The method of claim 1, wherein the cancer is non-small cell lung cancer.

7. The method of claim 1, wherein the cancer is prostate cancer.

8. The method of claim 7, wherein the prostate cancer is castration-resistant prostate cancer.

9. A method of treating cancer, wherein the cancer is selected from non-small cell lung cancer and prostate cancer, comprising administering to a patient in need of such treatment a tablet pharmaceutical composition comprising, based on 100 weight/weight percent:
30-32 percent by weight of Compound I, L-malate salt
wherein Compound I is:

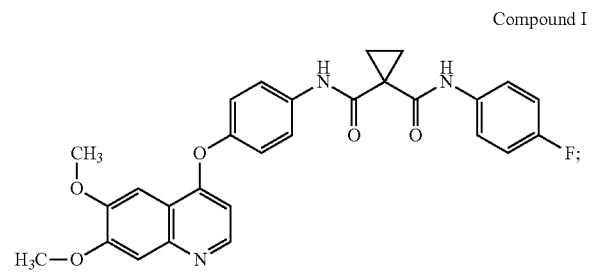 [SMILES: COc1cc2nccc(Oc3ccc(NC(=O)C4(C(=O)Nc5ccc(F)cc5)CC4)cc3)c2cc1OC]

Compound I 38-40 percent by weight of microcrystalline cellulose;
18-22 percent by weight of lactose;
2-4 percent by weight of hydroxypropyl cellulose;
4-8 percent by weight of croscarmellose sodium;
0.2-0.6 percent by weight of colloidal silicon dioxide; and
0.5-1 percent by weight of magnesium stearate;
and further comprising a film coating containing hypromellose, titanium dioxide, triacetin, and iron oxide yellow.

10. The method of claim 9, wherein the lactose in the tablet pharmaceutical composition is lactose anhydrous.

11. The method of claim 9, wherein the tablet pharmaceutical composition contains 20 to 100 mg of Compound I.

12. The method of claim 9, wherein the tablet pharmaceutical composition contains 20, 25, 50, 60, 75, 80, or 100 mg of Compound I.

13. The method of claim 9, wherein the cancer is non-small cell lung cancer.

14. The method of claim 9, wherein the cancer is prostate cancer.

15. The method of claim 14, wherein the prostate cancer is castration-resistant prostate cancer.

16. A method of treating cancer, wherein the cancer is selected from non-small cell lung cancer and prostate cancer, comprising administering to a patient in need of such treatment a tablet pharmaceutical composition comprising about:

| Ingredient | (% w/w) |
| --- | --- |
| Compound I, L-malate salt | 31.68 |
| Microcrystalline Cellulose | 38.85 |
| Lactose anhydrous | 19.42 |
| Hydroxypropyl Cellulose | 3.00 |
| Croscarmellose Sodium | 3.00 |
| Silicon dioxide, Colloidal | 0.30 |
| Magnesium Stearate | 0.75 |
| Total | 100.00 | wherein Compound I is:

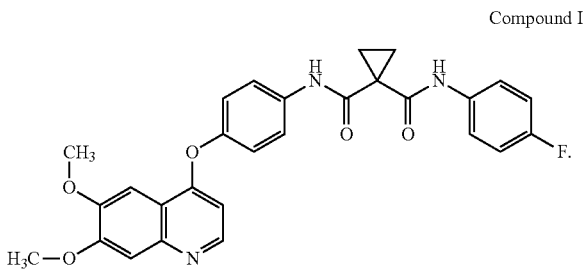 [SMILES: COc1cc2nccc(Oc3ccc(NC(=O)C4(C(=O)Nc5ccc(F)cc5)CC4)cc3)c2cc1OC]

Compound I

17. The method of claim 16, wherein the tablet pharmaceutical composition contains 20 to 100 mg of Compound I.

18. The method of claim 16, wherein the tablet pharmaceutical composition contains 20, 25, 50, 60, 75, 80, or 100 mg of Compound I.

19. The method of claim 16, wherein the cancer is non-small cell lung cancer.

20. The method of claim 16, wherein the cancer is prostate cancer.

21. The method of claim 20, wherein the prostate cancer is castration-resistant prostate cancer.

22. A method of treating cancer, wherein the cancer is selected from non-small cell lung cancer and prostate cancer, comprising administering to a patient in need of such treatment a tablet pharmaceutical composition comprising about:

| Ingredient | (% w/w) |
| --- | --- |
| Compound I, L-malate salt | 31.68 |
| Microcrystalline Cellulose | 38.85 |
| Lactose anhydrous | 19.42 |
| Hydroxypropyl Cellulose | 3.00 |
| Croscarmellose Sodium | 3.00 |
| Total Intra-granular | 95.95 |
| Silicon dioxide, Colloidal | 0.30 |
| Croscarmellose Sodium | 3.00 |
| Magnesium Stearate | 0.75 |
| Total | 100.00 | wherein Compound I is:

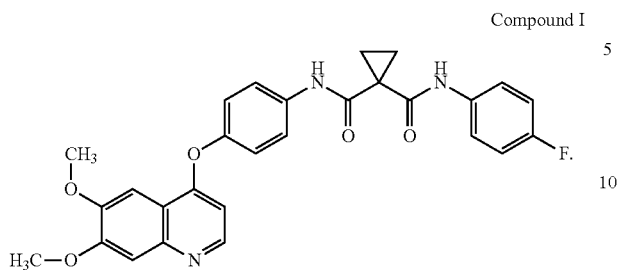

Compound I

23. The method of claim 22, wherein the tablet pharmaceutical composition contains 20 to 100 mg of Compound I.

24. The method of claim 22, wherein the tablet pharmaceutical composition contains 20, 25, 50, 60, 75, 80, or 100 mg of Compound I.

25. The method of claim 22, wherein the cancer is non-small cell lung cancer.

26. The method of claim 22, wherein the cancer is prostate cancer.

27. The method of claim 26, wherein the prostate cancer is castration-resistant prostate cancer.

* * * * *